US009820823B2

(12) United States Patent
Richmond et al.

(10) Patent No.: US 9,820,823 B2
(45) Date of Patent: Nov. 21, 2017

(54) GRIP FORCE CONTROL FOR ROBOTIC SURGICAL INSTRUMENT END EFFECTOR

(71) Applicant: INTUITIVE SURGICAL OPERATIONS, INC., Sunnyvale, CA (US)

(72) Inventors: Gregory F. Richmond, San Jose, CA (US); Gary S. Guthart, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 15/090,059

(22) Filed: Apr. 4, 2016

(65) Prior Publication Data
US 2016/0213437 A1 Jul. 28, 2016

Related U.S. Application Data

(62) Division of application No. 13/655,999, filed on Oct. 19, 2012, now Pat. No. 9,314,307.
(Continued)

(51) Int. Cl.
G05B 15/00 (2006.01)
G05B 19/00 (2006.01)
(Continued)

(52) U.S. Cl.
CPC ............ *A61B 34/37* (2016.02); *A61B 34/30* (2016.02); *A61B 2017/00022* (2013.01);
(Continued)

(58) Field of Classification Search
CPC ........ A61B 19/2203; A61B 2019/2223; A61B 2019/2234; A61B 2019/464; A61B 2019/223
(Continued)

(56) References Cited

U.S. PATENT DOCUMENTS 5,343,385 A * 8/1994 Joskowicz ............. B25J 9/1664
700/255
5,575,789 A 11/1996 Bell et al.
(Continued)

FOREIGN PATENT DOCUMENTS

EP 2332478 A2 6/2011
JP H08323664 A 12/1996
(Continued)

OTHER PUBLICATIONS

Extended European Search Report for Application No. 12841954.6, mailed on Oct. 19, 2015, 7 pages.
(Continued)

*Primary Examiner* — Harry Oh
(74) *Attorney, Agent, or Firm* — Jones Robb, PLLC

(57) ABSTRACT

A method of controlling an end effector of a robotically-controlled surgical instrument may include receiving a first input signal indicative of a high grip level input at a master grip input mechanism that controls a slave gripping force of the end effector; receiving a second input signal indicative of a user's readiness to operate the surgical instrument to perform a first surgical procedure; and outputting a locking signal in response to receiving the first input signal and the second input signal together to lock one or more degrees of freedom of the surgical instrument during the first surgical procedure.

24 Claims, 10 Drawing Sheets

Related U.S. Application Data

(60) Provisional application No. 61/550,356, filed on Oct. 21, 2011.

(51) Int. Cl.
*A61B 34/37* (2016.01)
*A61B 34/30* (2016.01)
*A61B 17/00* (2006.01)
*A61B 90/00* (2016.01)
*A61B 34/00* (2016.01)

(52) U.S. Cl.
CPC ............ *A61B 2017/00199* (2013.01); *A61B 2017/00238* (2013.01); *A61B 2034/254* (2016.02); *A61B 2034/301* (2016.02); *A61B 2090/031* (2016.02)

(58) Field of Classification Search
USPC .................................. 606/130; 700/245–264
See application file for complete search history.

(56) References Cited

U.S. PATENT DOCUMENTS

| | | | |
|---|---|---|---|
| 5,876,325 A * | 3/1999 | Mizuno | A61B 1/00048 600/102 |
| 6,132,368 A * | 10/2000 | Cooper | A61B 46/13 600/102 |
| 6,256,556 B1 | 7/2001 | Zenke | |
| 6,312,435 B1 * | 11/2001 | Wallace | A61B 34/70 606/130 |
| 6,348,911 B1 | 2/2002 | Rosenberg et al. | |
| 6,424,885 B1 * | 7/2002 | Niemeyer | A61B 34/70 600/109 |
| 6,459,926 B1 * | 10/2002 | Nowlin | A61B 34/70 600/102 |
| 6,522,906 B1 * | 2/2003 | Salisbury, Jr. | A61B 8/12 600/102 |
| 6,592,315 B2 | 7/2003 | Osborne, Jr. | |
| 6,594,552 B1 | 7/2003 | Nowlin et al. | |
| 6,659,939 B2 * | 12/2003 | Moll | A61B 19/2203 600/102 |
| 6,697,664 B2 | 2/2004 | Kienzle et al. | |
| 6,817,974 B2 | 11/2004 | Cooper et al. | |
| 7,125,403 B2 * | 10/2006 | Julian | A61B 17/00234 606/1 |
| 7,166,114 B2 | 1/2007 | Moctezuma De La Barrera et al. | |
| 7,209,803 B2 | 4/2007 | Okamoto et al. | |
| 7,386,365 B2 | 6/2008 | Nixon | |
| 8,184,880 B2 * | 5/2012 | Zhao | G06K 9/6211 345/419 |
| 8,226,575 B2 | 7/2012 | Levy | |
| 8,375,808 B2 * | 2/2013 | Blumenkranz | B25J 15/0009 73/862.044 |
| 8,527,094 B2 * | 9/2013 | Kumar | A61B 34/37 600/101 |
| 8,830,224 B2 * | 9/2014 | Zhao | G06T 7/0075 345/419 |
| 8,852,174 B2 * | 10/2014 | Burbank | A61B 19/2203 606/1 |
| 8,935,003 B2 * | 1/2015 | Itkowitz | A61B 19/2203 700/245 |
| 8,945,095 B2 * | 2/2015 | Blumenkranz | A61B 19/2203 606/1 |
| 9,043,027 B2 | 5/2015 | Durant et al. | |
| 9,314,307 B2 | 4/2016 | Richmond et al. | |
| 2001/0034530 A1 | 10/2001 | Malackowski et al. | |
| 2002/0042620 A1 * | 4/2002 | Julian | A61B 17/00234 606/130 |
| 2002/0045905 A1 * | 4/2002 | Gerbi | A61B 17/34 606/108 |
| 2006/0030840 A1 * | 2/2006 | Nowlin | B25J 9/1689 606/1 |
| 2006/0095143 A1 | 5/2006 | Sunaoshi | |
| 2006/0142657 A1 * | 6/2006 | Quaid | A61N 1/372 600/424 |
| 2006/0184279 A1 | 8/2006 | Okamoto et al. | |
| 2007/0032906 A1 * | 2/2007 | Sutherland | A61B 19/22 700/248 |
| 2008/0114494 A1 * | 5/2008 | Nixon | B25J 9/1692 700/254 |
| 2008/0154246 A1 | 6/2008 | Nowlin et al. | |
| 2008/0188749 A1 * | 8/2008 | Rasche | A61B 8/0833 600/443 |
| 2009/0012532 A1 | 1/2009 | Quaid et al. | |
| 2009/0036902 A1 * | 2/2009 | DiMaio | A61B 19/2203 606/130 |
| 2009/0088774 A1 | 4/2009 | Swarup et al. | |
| 2009/0088775 A1 | 4/2009 | Swarup et al. | |
| 2009/0131941 A1 * | 5/2009 | Park | A61B 17/154 606/87 |
| 2010/0010505 A1 * | 1/2010 | Herlihy | A61B 90/11 606/130 |
| 2010/0153317 A1 | 6/2010 | Lee | |
| 2010/0228264 A1 | 9/2010 | Robinson et al. | |
| 2010/0234857 A1 * | 9/2010 | Itkowitz | G09B 23/285 606/130 |
| 2010/0256558 A1 | 10/2010 | Olson et al. | |
| 2011/0087238 A1 * | 4/2011 | Wang | B25J 9/1689 606/130 |
| 2011/0106141 A1 * | 5/2011 | Nakamura | A61B 34/71 606/205 |
| 2011/0108569 A1 | 5/2011 | Jones et al. | |
| 2011/0118748 A1 * | 5/2011 | Itkowitz | A61B 19/2203 606/130 |
| 2011/0130761 A1 * | 6/2011 | Plaskos | A61B 17/155 606/87 |
| 2011/0144806 A1 | 6/2011 | Sandhu et al. | |
| 2011/0306986 A1 | 12/2011 | Lee et al. | |
| 2012/0083801 A1 | 4/2012 | Nixon | |
| 2012/0109150 A1 | 5/2012 | Quaid et al. | |
| 2012/0150154 A1 | 6/2012 | Brisson et al. | |
| 2012/0185090 A1 | 7/2012 | Sanchez et al. | |
| 2012/0215220 A1 | 8/2012 | Manzo et al. | |
| 2012/0255986 A1 * | 10/2012 | Petty | A61B 17/072 227/176.1 |
| 2012/0283745 A1 | 11/2012 | Goldberg et al. | |
| 2012/0310221 A1 | 12/2012 | Durant et al. | |
| 2012/0310254 A1 | 12/2012 | Manzo et al. | |
| 2012/0310255 A1 | 12/2012 | Brisson et al. | |
| 2012/0310256 A1 | 12/2012 | Brisson | |
| 2012/0316573 A1 * | 12/2012 | Durant | A61B 19/2203 606/130 |
| 2013/0035790 A1 | 2/2013 | Olivier, III et al. | |

FOREIGN PATENT DOCUMENTS

| | | |
|---|---|---|
| JP | 2009107074 A | 5/2009 |
| JP | 2010182235 A | 8/2010 |
| JP | 2011183460 A | 9/2011 |
| WO | WO-2006087689 A2 | 8/2006 |
| WO | WO-2007034161 A2 | 3/2007 |
| WO | WO-2010025338 A1 | 3/2010 |
| WO | WO-2010109932 A1 | 9/2010 |
| WO | WO-2011125007 A1 | 10/2011 |

OTHER PUBLICATIONS

International Search Report and Written Opinion for Application No. PCT/IS2012/040034, mailed on Nov. 27, 2012, 15 pages.
International Search Report and Written Opinion for Application No. PCT/US2012/061093, mailed Feb. 25, 2013, 10 pages.
U.S. Appl. No. 61/491,698, filed May 31, 2011.
U.S. Appl. No. 61/491,647, filed May 31, 2011.
U.S. Appl. No. 61/491,804, filed May 31, 2011.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

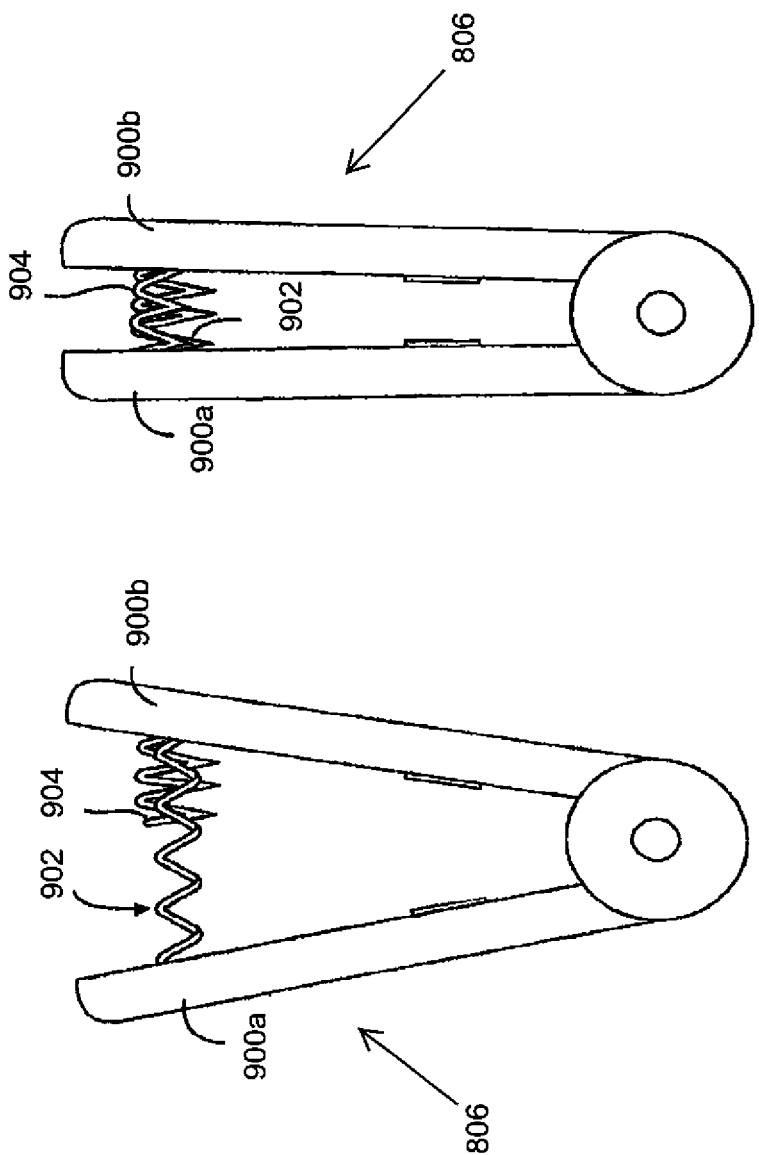

GRIP FORCE CONTROL FOR ROBOTIC SURGICAL INSTRUMENT END EFFECTOR

CROSS-REFERENCE TO RELATED APPLICATIONS

This application is a divisional of U.S. patent application Ser. No. 13/655,999, filed on Oct. 19, 2012, which claims the benefit of priority of U.S. Provisional Application No. 61/550,356, filed Oct. 21, 2011, the entire contents of each of which is incorporated by reference herein in its entirety.

TECHNICAL FIELD

The present disclosure is generally directed to controlling a surgical instrument end effector. More particularly, aspects of the present disclosure relate to controlling the gripping force of an end effector for a robotically-controlled surgical instrument.

INTRODUCTION

Minimally invasive surgical techniques generally attempt to perform surgical procedures while minimizing damage to healthy tissue. Robotically-controlled surgical instruments can be used to perform various minimally invasive surgical procedures remotely. In such systems, surgeons manipulate various input devices at a surgeon console (sometimes referred to herein as master inputs). The input at the surgeon console is communicated to a patient side cart that interfaces with one or more robotically-controlled surgical instruments, where teleoperated/telerobotic manipulation of the surgical instrument occurs to perform a surgical and/or other procedure on the patient.

Minimally invasive, robotically-controlled surgical instruments may be used in a variety of operations and have various configurations. Many such instruments include a surgical end effector mounted at a distal end of a long shaft that is configured to be inserted (e.g., laporoscopically or thoracoscopically) through an opening (e.g., body wall incision, natural orifice) to reach a remote surgical site within a patient. In some instruments, an articulating wrist mechanism is mounted to the distal end of the instrument's shaft to support the end effector and alter an orientation (e.g., pitch and/or yaw) of the end effector with reference to the shaft's longitudinal axis.

Telerobotically controlled end effectors may be configured to perform various functions, including any of a variety of surgical procedures that are conventionally performed in either open or manual minimally invasive surgical procedures. Examples include, but are not limited to, sealing, cutting, cauterizing, ablating, suturing, stapling, etc. The end effectors may include a gripping device, such as jaws or blades, in cases in which tissue may need to be grasped and held as a procedure is performed, for example, during sealing (e.g., via cauterizing) or cutting of the tissue. In some instances, the control of the gripping device of a surgical instrument end effector occurs through master grip input from a surgeon at the surgeon console. To control motion of an end effector, servo-actuators (e.g., servo motors), can be used to transmit force or torque to various components that ultimately transmit from a transmission mechanism that interfaces with the patient side manipulator down the shaft and to the end effector.

In some cases, when using a surgical instrument that includes an end effector having a gripping device, it may be desirable to use the gripping device to move tissue and/or other material at the surgical site by gripping the same with the gripping device. When using a gripping device in such a manner, it may be desirable to use less gripping force in comparison to a gripping force that may be desired to achieve another surgical procedure, such as, for example, sealing and/or cutting. For example, lower gripping forces may be desirable when using the gripping device to move tissue and/or other body parts/materials around so as to minimize the risk of damaging the same. On the other hand, higher gripping forces may be desirable when using the gripping device for other procedures. For example, if the gripping force is not high enough during a procedure such as cutting, a translating blade used to cut transversely through the tissue could push the tissue distally instead of cutting all the way through the tissue. Likewise, if the gripping force is not high enough during a procedure such as sealing (e.g., cauterizing), for example, effective contact for sealing of tissue surfaces (e.g., opposing wall portions of a vessel) may not be achieved.

The user may indicate that a higher gripping force is to be used by, for example, squeezing a gripping input mechanism that controls the gripping force at the end effector. The user may inadvertently squeeze the gripping input mechanism too hard, resulting in a higher gripping force at the end effector during operations of the end effector in which a higher gripping force is not desired. For example, prior to or after performing a procedure that requires a higher gripping force, such as sealing or cutting, the user may squeeze the gripping input mechanism hard enough to result in higher gripping forces at the end effector. Using higher gripping forces during operations that do not require higher gripping forces, such as while the user is manipulating tissue prior to or after performing a sealing or cutting procedure, can lead to undesirable and/or unintentional movements. For example, undesired pitch or yaw motions may occur as the end effector rolls. In addition, unintentional and/or unsteady movement of the end effector may occur during the high grip force action due to movement in one of pitch/yaw by a wrist, roll of the shaft, and/or translation along the shaft. Such movement instability of the end effector can negatively impact the desired surgical procedure.

There exists a need, therefore, to provide gripping force control of a surgical instrument end effector gripping device in order to address the various issues faced when performing robotically-controlled surgical procedures that rely on relatively high gripping forces by such an end effector.

SUMMARY

The present disclosure solves one or more of the above-mentioned problems and/or demonstrates one or more of the above-mentioned desirable features. Other features and/or advantages may become apparent from the description that follows.

In accordance with at least one exemplary embodiment, the present teachings contemplate a method of controlling a gripping force of an end effector of a robotically-controlled surgical instrument. The method includes receiving a first input signal indicative of a high grip level input at a master gripping mechanism that controls a slave gripping force of the end effector; receiving a second input signal indicative of a user's readiness to operate the surgical instrument to perform a surgical procedure; and outputting an actuation signal in response to receiving the first input signal and the second input signal together to increase the slave gripping force from a first level to a second level higher than the first level during the surgical procedure.

Additional objects and advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the invention, as disclosed or claimed. The claims should be entitled to their full breadth of scope, including equivalents.

BRIEF DESCRIPTION OF THE DRAWINGS

The present disclosure can be understood from the following detailed description either alone or together with the accompanying drawings. The drawings are included to provide a further understanding of the present disclosure, and are incorporated in and constitute a part of this specification. The drawings, which are incorporated in and constitute a part of this specification, illustrate one or more embodiments of the present disclosure and, together with the description, serve to explain certain principles and operation. In the drawings.

FIG. 9A is a side view of a master grip input mechanism in an open position in accordance with an exemplary embodiment; and FIG. 9B is a side view of a master grip input mechanism in a closed position in accordance with an exemplary embodiment.

DETAILED DESCRIPTION

Figure 1A:
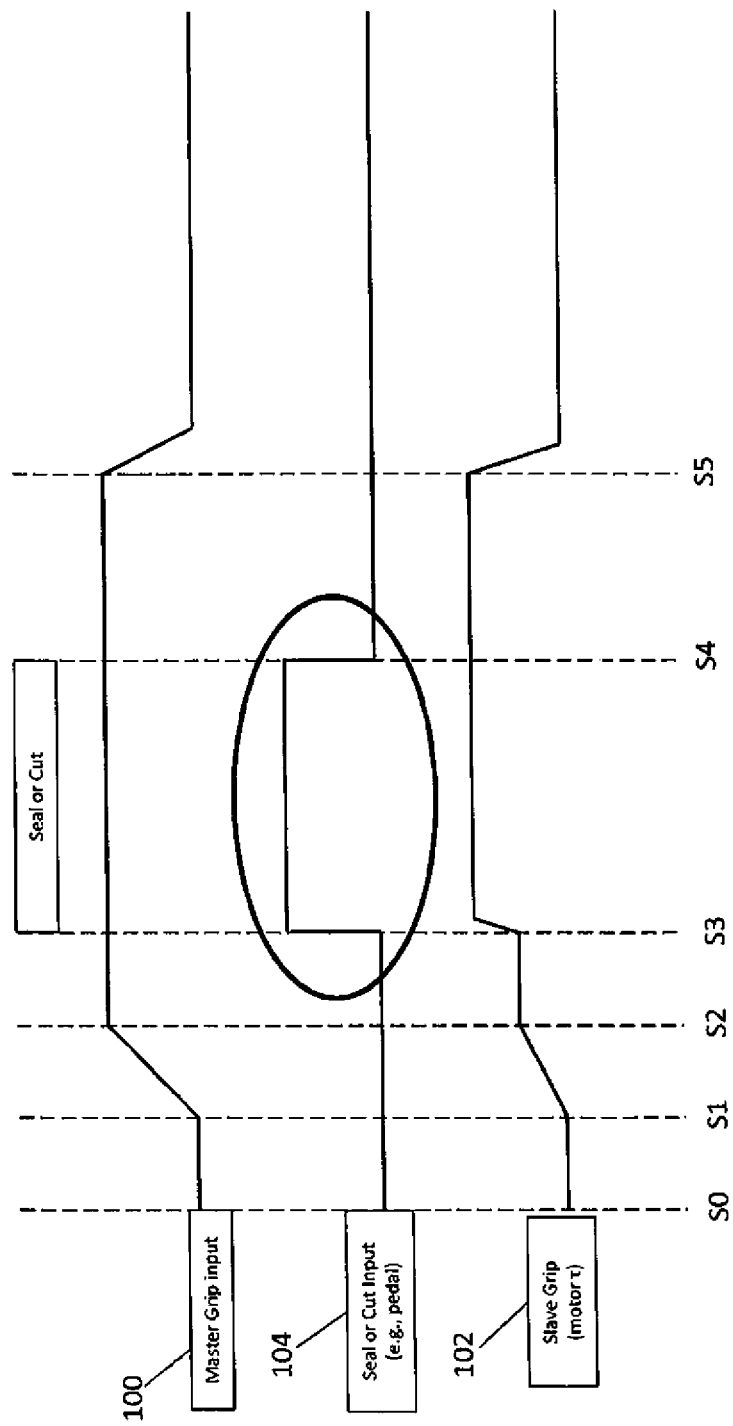
FIG. 1A is a state diagram depicting a gripping force control scheme for a robotically-controlled surgical instrument in accordance with at least one exemplary embodiment.

This description and the accompanying drawings illustrate exemplary embodiments and should not be taken as limiting, with the claims defining the scope of the present disclosure, including equivalents. Various mechanical, compositional, structural, electrical, and operational changes may be made without departing from the scope of this description and the invention as claimed, including equivalents. In some instances, well-known structures, and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or the electrosurgical instrument.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates controlling a robotically-controlled surgical instrument end effector gripping device such that a relatively lower or higher gripping force may be exerted by the gripping device, depending upon the application involved as indicated by input received at a surgeon console. For example, for procedures such as grasping and moving tissue and/or other material (e.g., body structures) at a surgical site, the end effector gripping device may be controlled to exert a relatively lower gripping force to allow the tissue to be grasped and moved without unnecessarily damaging the tissue. On the other hand, for procedures such as, for example, sealing or cutting, the end effector gripping device may be controlled to exert a higher gripping force sufficient to hold the tissue relatively firmly to effectively perform the desired surgical procedure that is implemented with a relatively high gripping force. Various exemplary embodiments, therefore, provide an automatic control technique of an end effector gripping device to elevate and hold the gripping force at relatively higher levels during the appropriate procedures and lower levels during other procedures in which the high gripping force is not necessary and may not be desirable.

In addition, in order to avoid instability of the surgical instrument end effector due to the higher gripping force that occur when the user grips a master gripping input mechanism beyond a gripping force threshold, various exemplary embodiments limit the higher gripping force from occurring when the operation that necessitates the higher gripping force is not being performed. In particular, in accordance with various exemplary embodiments, in order to constrain the higher gripping force only to the procedure that requires the higher gripping force, a method of controlling a gripping force of an end effector provides a higher gripping force based on two inputs from a surgeon—the first input being indicative of a higher gripping level input by the user at a surgeon master gripping input and the second input being indicative of the user's readiness to operate the surgical instrument to perform a surgical procedure that utilizes the relatively higher gripping force of the end effector. In accordance with various exemplary embodiments, the gripping force of the end effector (slave grip force) is controlled by altering or limiting a torque of an electric motor (e.g., servo motor) at the patient side cart that interfaces with a drive input of a transmission mechanism associated with the surgical instrument.

In addition, various exemplary embodiments provide a method of locking (i.e., preventing actuation) one or more degrees of freedom of the end effector during certain surgical procedures to provide a higher level of stability while the procedure is being performed.

Although the exemplary embodiments and description below focus mainly on controlling gripping force of a surgical instrument during sealing and cutting procedures, the principles of the exemplary embodiments could be applied to other surgical procedures, including but not limited to, for example, clamping of a vessel or other hollow body structure, cutting tissue using pivoting blades of an end effector, surgically stapling tissue, and/or other procedures where a relatively high gripping force may be desirable. For some of these instruments and associated procedures, the relatively high end effector gripping force is generated by a servo motor torque that is higher than the highest motor torque normally used to operate other jawed instruments, such as surgical shears, tissue graspers, needle drivers, and the like.

Figure 6:
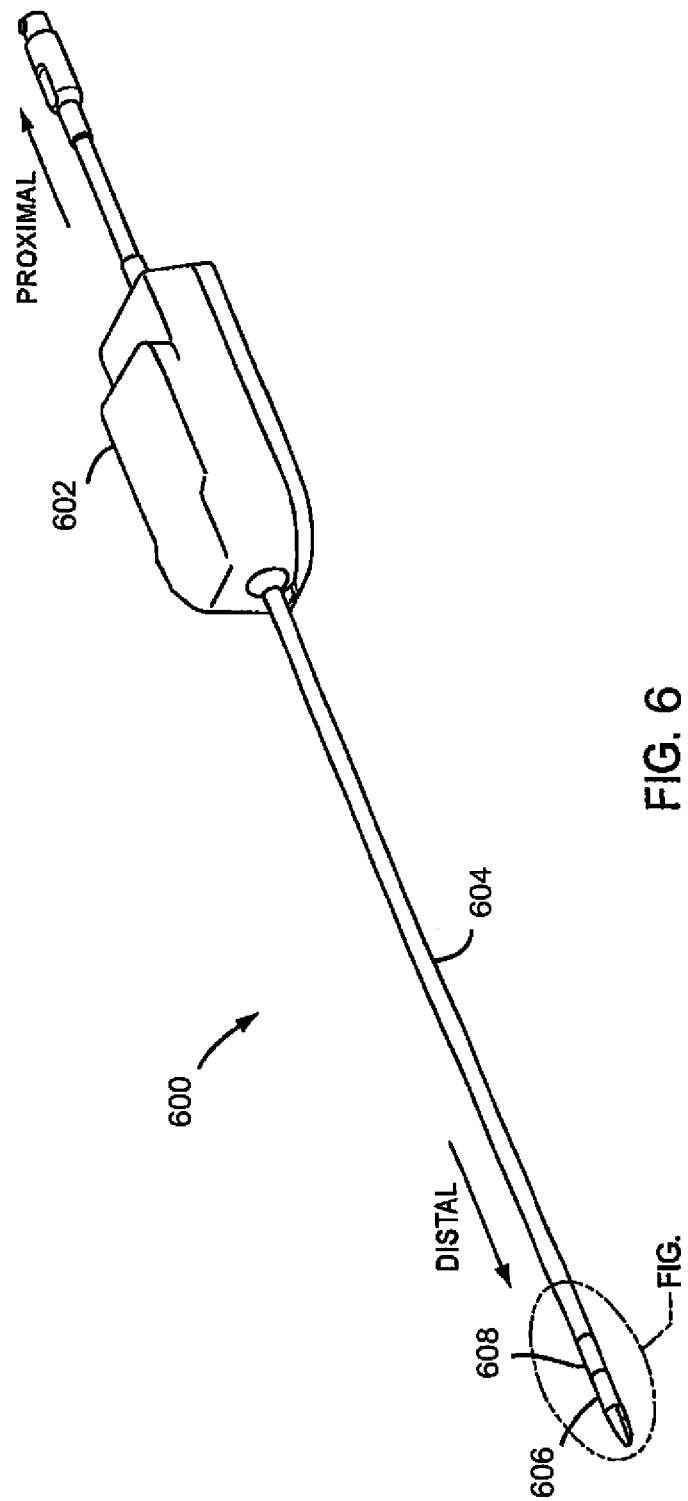
FIG. 6 is a perspective view of a robotically-controlled surgical instrument in accordance with at least one exemplary embodiment.
Figure 7:
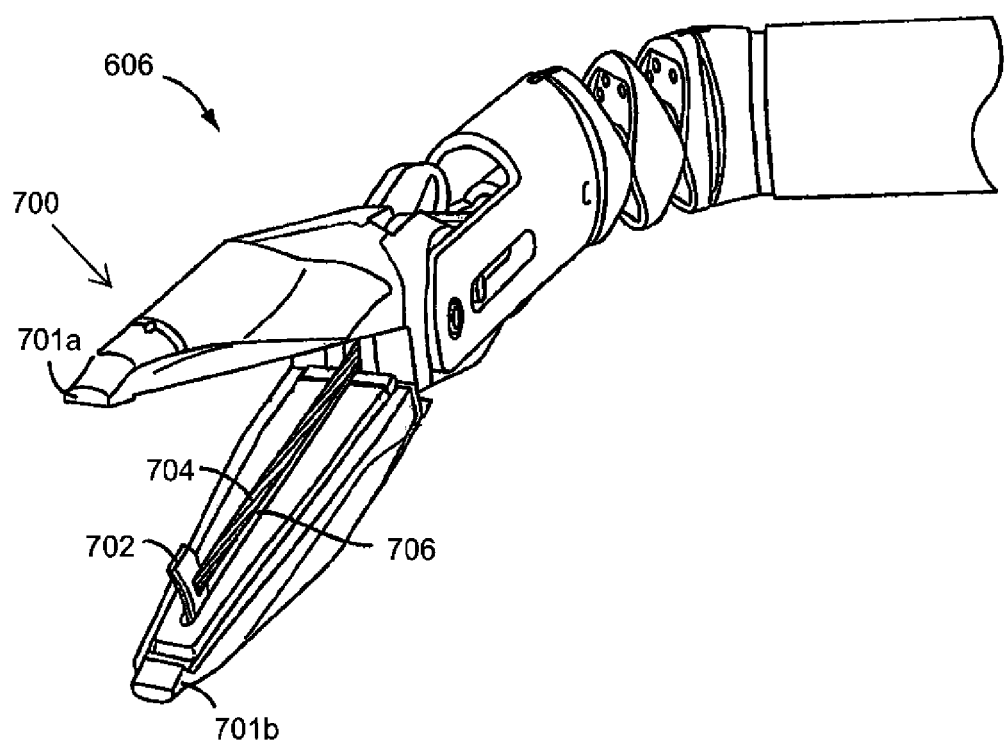
FIG. 7 is a detailed view of an exemplary end effector corresponding to a portion of the surgical instrument of FIG. 6 in accordance with an exemplary embodiment.

With reference to FIG. 6, an exemplary embodiment of a robotically-controlled surgical instrument 600 is depicted. FIG. 6 is a perspective view of the surgical instrument 600, and FIG. 7 is a detailed view of an exemplary, non-limiting embodiment of the corresponding portions denoted in FIG. 6 that the surgical instrument 600 can include. The directions "proximal" and "distal" are used herein to define the directions as shown in FIG. 6, with distal generally being in a direction further along a kinematic arm or closest to the surgical work site in the intended operational use of the instrument 600, for example, in use for performing surgical procedures. The "proximal" and "distal" directions as used herein are labeled on FIG. 6. As shown in FIG. 6, the instrument 600 generally includes a force/torque drive transmission mechanism 602 at its proximal end, an instrument shaft 604 mounted to the transmission mechanism 602, and an end effector 606 disposed at the distal end of the shaft 604. In the exemplary embodiment shown in FIG. 6, the surgical instrument 600, a portion of which is shown in more detail in FIG. 7, also includes an optional articulating wrist mechanism 608 mounted at the distal end of the shaft 604 to support the end effector 606 and change its orientation with reference to the shaft's 604 longitudinal axis.

Figure 8:
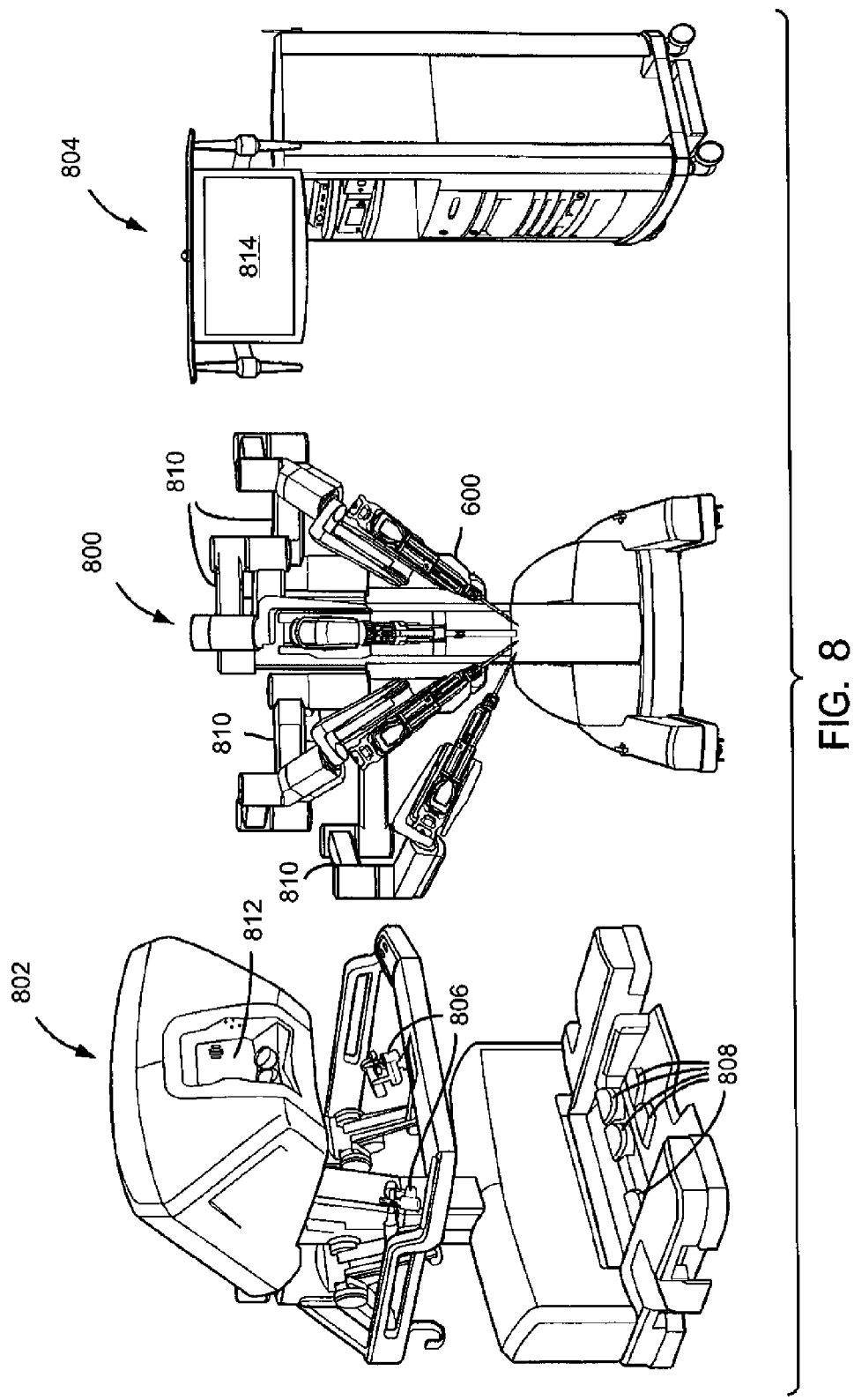
FIG. 8 is a diagrammatic view of an exemplary robotic surgical system configured to operate a robotically-controlled surgical instrument in accordance with at least one exemplary embodiment.

In an exemplary embodiment, the instrument 600 is configured to be mounted on and used with a minimally invasive robotic surgical system, which in an exemplary embodiment includes a patient side cart 800, a surgeon console 802, and an electronics/control console 804, as illustrated in a diagrammatic view of FIG. 8 (it is noted that the system components in FIG. 8 are not shown in any particular positioning and can be arranged as desired, with the patient side cart being disposed relative to the patient so as to effect surgery on the patient). A non-limiting, exemplary embodiment of a robotic surgical system with which the instrument 600 can be utilized is a da Vinci® Si (model no. IS3000) commercialized by Intuitive Surgical, Inc. of Sunnyvale, Calif.

The robotic surgical system is used to perform minimally invasive robotic surgery by interfacing with and controlling a variety of surgical instruments, as those of ordinary skill in the art are generally familiar. The patient side cart 800 includes various arms 810 for holding, positioning, and manipulating various tools. As shown in FIG. 8, one arm 810 is configured to interface with and control a robotically-controlled surgical instrument 600, including an end effector 606. In general, the surgeon console 802 receives inputs from a surgeon by various input devices, including but not limited to, grip input levers 900a, 900b of a master grip input mechanism 806 and foot pedals 808, etc., and serves as a master controller by which the patient side cart 800 acts as a slave to implement the desired motions of the surgical instrument(s) (e.g., instrument 600) interfaced therewith, and accordingly perform the desired surgical procedure. The patient side cart 800 can include a plurality of jointed arms 810 configured to hold various tools, including, but not limited to, for example, a surgical instrument with an end effector (e.g., surgical instrument 600), and an endoscope (not shown). An electronic data processing system, including a processing device, and which may be provided at one or more of the surgeon console 802, the electronics/control console 804 and the patient side cart 800, may receive and process inputs from the surgeon console 802 and control the manipulation of the surgical instrument 600 at the patient side cart 800 based on the inputs received at the surgeon console 802. However, the present disclosure is not limited to receiving inputs at the surgeon console 802, and inputs may be received at any device which results in manipulation of an end effector of the surgical instrument 600. The surgical instrument 600 may be manipulated at the patient side cart 800, or alternatively, may be manipulated in combination with any other type of surgical instrument support device, or entirely separately from a support device, as a result of inputs received from the user, e.g., the surgeon.

In various exemplary embodiments, inputs from the surgeon console 802 or from input units otherwise accessible to a surgeon can be provided to the controller(s) via various master input devices, such as, for example, one or more pedals 808, and one or more hand-held grip input levers 900a, 900b.In various exemplary embodiments described herein, the pedals 808 may be used to send signals to perform a sealing and/or cutting operation of the robotically controlled surgical instrument 600 and the hand-held grip input levers 900a, 900b may be used to send signals to control movement of the wrist 608 (e.g., pitch/yaw movement), the instrument shaft 604 (e.g., roll and/or translation), and/or opening and closing (gripping) movement of an end effector gripping device (e.g., jaws or blades). Those having ordinary skill in the art are familiar with the general use of such teleoperated robotic surgical systems to provide input from a surgeon at a surgeon console to ultimately effect operation of a surgical instrument interfacing with a patient side cart.

Based on the master inputs at the surgeon console 802, the patient side cart 800 can interface with the transmission mechanism 602 of the surgical instrument 600 to position and actuate the instrument 600 to perform a desired medical procedure. For example, based on the master inputs from the surgeon console 802, the transmission mechanism 602, which includes various torque/drive input mechanisms (e.g., in the form of drive disks) configured to be driven via teleoperated servo actuators (e.g., motors) associated with the patient side cart 800, can transmit the inputs into various forces and/or torques to ultimately actuate (drive) the overall instrument 600 to perform a surgical procedure. For example, master inputs from the surgeon console 802 can be converted at the patient side cart 800 through the transmission mechanism 602 to roll shaft 604, articulate the wrist 608 relative to the shaft (e.g., in pitch and/or yaw), and/or to open and close the gripping device 700 (see FIG. 7).

The electronics/control console 804, which may include, for example, an electrosurgical processing unit, receives and transmits various control signals to and from the patient side cart 800 and the surgeon console 802, and can transmit light and process images (e.g., from an endoscope at the patient side cart 800) for display, such as, for example, display 812 at the surgeon console 802 and/or on a display 814 associated with the electronics/control console 804. Those having ordinary skill in the art are generally familiar with such electronics/control consoles of robotically controlled surgical systems.

The patient side cart 800 is positioned proximate to a patient and the surgical instrument 600 is used to perform various surgical procedures at a work site in the patient's body through the use of the remotely actuated end effector 606. Exemplary surgical procedures that the end effector 606 can perform include, but are not limited to, for example, clamping of a vessel or other hollow body structure, cutting tissue using pivoting blades of an end effector, and/or other procedures where a relatively high gripping force may be desirable.

With reference now to FIG. 7, an exemplary embodiment of an end effector 606 of the instrument 600 is shown, although the end effector 606 is not limited thereto and may be any end effector configured for use to perform surgical procedures that utilize gripping forces. The end effector 606 may be provided with a gripping device 700, such as, for example, opposing jaws 701a, 701b or gripping blades (e.g., similar to scissors), provided at the end effector 606. The jaws 701a, 701b are configured to move to and from an open position and a closed position. In the closed position, the jaws 701a, 701b can grip material, such as tissue and the like. In an exemplary embodiment, the jaws 701a, 701b can deliver electrosurgical energy, for example via electrodes provided on opposing faces of the jaws 701a, 701b, sufficient to seal (e.g., cauterize) tissue together. In addition, the end effector 606 may also include a cutting element in the form of a short cutting blade 702 attached to a cable 704. The cutting blade 702 may be received in a groove 706 of the bottom jaw 701b and operable to traverse in proximal and distal directions along a length of the jaws 701a, 701b to perform a cutting operation. While FIG. 7 shows an example of an end effector that may be used during operation of the gripping force control method, it is to be understood by those of ordinary skill in the art that any type of end effector may be used in which a relatively high gripping force is used during the implementation of a surgical procedure, such as, for example, cutting or sealing. For more details regarding an exemplary embodiment of a surgical instrument and end effector with which gripping force control according to the present disclosure may be implemented, reference is made to U.S. Provisional Patent Application No. 61/491,698 (filed on May 31, 2011; entitled surgical instrument with motor), the entire contents of which are incorporated herein by reference.

With reference now to FIGS. 1A-1B, and 2-4, event-based state diagrams are shown which illustrate exemplary methods of controlling the gripping force of the end effector 606 of the surgical instrument 600. The state diagrams illustrate elements S0-Sn (where n=1, 2, 3, . . . ). Elements S0-Sn illustrate the occurrence of events and are not necessarily intended to correspond with periods of time. Elements S0-Sn do not necessarily correspond to the same occurrences in each of the state diagrams and are to be read independently of one another, depending on the individual state diagram. However, one of ordinary skill in the art would understand that elements S0-Sn may relate to times at which each of the events occurs. At S0, prior to the user, e.g., a surgeon, exerting actuating force on master grip input levers 900a, 900b of a master grip input mechanism 806 at the surgeon console 802, the master grip input signal 100 is in an "off" state. Also, the gripping force (e.g., slave grip 102) of the gripping device 701 is in an "off" state at S0. As described above, in an exemplary embodiment, therefore no torque is provided by the teleoperated servo motor that controls the opening/closing (gripping) of the jaws 701a, 701b. Further, a procedure input 104 indicative of the user's command to cause a surgical procedure relying on a relatively high gripping force (e.g., sealing or cutting) to be performed at the end effector 606 of the surgical instrument 600 is not received, and thus the seal or cut procedure input 104 is indicated to be in an off state in the state diagram of FIG. 1A.

When the user at the surgeon console 802 is ready to perform a procedure using the gripping device 700, e.g., jaws 701a, 701b, at S1 the user manipulates a master grip input mechanism 806 at the surgeon console 802. For example, the surgeon may squeeze grip levers 900a, 900b together. However, the master grip input is not limited thereto and may be an input other than squeezing the gripping levers 900a, 900b together that provides an indication from a user, e.g., a surgeon, that the user desires a high slave gripping force at the end effector. In an exemplary embodiment, for example, the master grip input may be a user pressing one or more of the pedals 808.

In various exemplary embodiments, as depicted in the diagrammatic view of FIGS. 9A and 9B, a so-called "bumper" mechanism may be used to increase the resistance against squeezing the levers 900a, 900b together that the user experiences as two grip levers 900a, 900b are brought closer together. As shown in FIGS. 9A and 9B, as the grip levers 900a, 900b are brought into closer contact, a biasing transition mechanism including, for example, a first biasing mechanism, such as, for example, a first coiled spring 902 (shown in FIGS. 9A-9B), a magnet, etc., and a second biasing mechanism, such as, for example, a second coiled spring 904, a magnet, etc. provides haptic feedback to the user to provide an indication of squeezing against a first level of resistance. Compression of the first biasing mechanism 902 may indicate a lower gripping input range, while compression of the second biasing mechanism 904 may indicate a higher gripping input range. In an exemplary embodiment, the second biasing mechanism, for example, second coiled spring 904 (see FIGS. 9A-9B) may have a greater stiffness than the first biasing mechanism, e.g., first spring 902. In an alternative exemplary embodiment, the biasing system may rely on a single variable rate spring where portions of the variable rate spring correspond to the first biasing mechanism and the second biasing mechanism, rather than the two different springs shown in FIGS. 9A and 9B. For examples of biasing mechanisms, reference is made to U.S. Pat. No. 6,594,552 (issued Jul. 15, 2003; entitled "GRIP STRENGTH WITH TACTILE FEEDBACK FOR ROBOTIC SURGERY"), the entire contents of which are incorporated by reference herein.

The biasing transition mechanism can provide the user with feedback that the gripping device of the end effector is transitioning from a relatively lower gripping force to a relatively higher gripping force. When the master grip input 100 is initiated at S1, and a master grip input signal is generated, the torque of the motor that ultimately controls the gripping force (slave grip 102) of the corresponding gripping device 700, such as jaws 701*a*, 701*b*, begins to increase to provide a gripping force to the gripping device 700. In another embodiment, the motor may actuate a clutch mechanism, which actuates the gripping of the end effector. As the master grip input signal 100 increases between S1 to S2, the corresponding force of the slave grip 102 increases from zero gripping force at S1 to a low gripping force at S2.

At S2, the master grip input signal 100 reaches a squeezing force threshold that corresponds to a predetermined, high grip level at the master grip input mechanism 806. In various exemplary embodiments, the squeezing force threshold may correspond to any input at the master grip, such as, for example, actuating the grip levers 900*a*, 900*b* of the master grip input mechanism 806 beyond some threshold level of actuation, e.g., beyond a threshold range of motion of the grip levers 900*a*, 900*b* toward one another, that may indicate that a higher slave gripping force is desired at the end effector 606. In another exemplary embodiment, when a mechanism is used to provide haptic feedback to the user, such as in FIGS. 9A-9B, the compression amount may correspond to a compression amount into a higher gripping force input range, for example, approximately 80% compression applied to the second biasing mechanism or 80% compression applied to the portion of the variable rate spring corresponding to a second biasing mechanism. That is, the actuation threshold may be indicated by, for example, the compression of the second biasing mechanism, such as second spring 904, to a point that is indicative of the user's intent to apply the higher gripping, rather than a repositioning or shifting of the user's grip. For example, a compression of the second biasing mechanism to a point 80% to 100% of the fully closed/actuated position, may be indicative of an intentional compression by the user. It should be understood that the actuation threshold range is exemplary, and a specific range may be chosen based on the type of procedure, the type of grip used, the type of biasing mechanism used, and other factors.

One of ordinary skill in the art would recognize that the present disclosure is not limited to the biasing mechanisms described and any of a variety of biasing devices or gripping level indicators may be used. Regardless of the configuration of the biasing mechanism, when the master grip input mechanism 806 includes biasing mechanisms, the master grip input mechanism 806, such as gripping levers 900*a*, 900*b*, provides feedback to the user to indicate a lower gripping input level and a higher gripping input level. In addition, as above, the system recognizes that a higher gripping input level is achieved when the squeezing force threshold at the master grip input mechanism 806 is reached, and at this point, the master grip input signal 100 is at a relatively high gripping input level.

Setting the squeezing force threshold to correspond to a relatively high amount of the compression of the second biasing mechanism can help to ensure that the user is intending to provide a higher level of grip of the master grip input mechanism 806, e.g., by providing feedback to the user. This can provide an additional safety feature to assist in preventing the user from increasing the master gripping force, and consequently the slave gripping force, to too high a level when the user is not intending for that level to be used.

As shown in FIG. 1A, in response to the user actuating the master grip input mechanism 806 (e.g., grip levers), according to some embodiments, the motor torque (and consequently slave grip force 102) also increases, thereby increasing the gripping force of the gripping device, indicated by zero slave gripping force at S1 increased to a low gripping force at S2. In other embodiments, the motor actuates a clutch mechanism at the force/torque drive transmission mechanism 602, which causes the slave gripping force. At S2, a relatively low slave gripping force is output. In various exemplary embodiments, the relatively low end effector grip actuation torque output at S2 may be, for example, about 0.3 Nm.

From S0 through S2, the procedure input 104, e.g., a sealing, cutting or stapling procedure, is not received and the procedure input is in an off state. At S3, an input indicative of a user's desire for the end effector 606 to perform a surgical procedure that relies on a relatively high gripping force is received, indicated in the state diagram as procedure input 104 transitioning from an off state to an on state. The surgical procedure to be performed may be one or more of, for example, a sealing procedure, a cutting procedure, etc. However, it is to be understood that these procedures are merely meant to be exemplary and any other type of procedure that would be implemented using a high gripping force by an end effector gripping device may be indicated by actuation of the input devices, such as pedals 808.

At S3, when both the master grip input signal 100 has reached the squeezing force threshold level and an additional input has been received at a procedure input device, such as one or more pedals 808, at the surgeon console 802, indicating that the high gripping force procedure is to be performed, i.e., the procedure input 104 is in an on state, then the motor torque and corresponding slave gripping force 102 is increased from the relatively low levels shown between S2 and S3, to the relatively higher levels depicted at S3. In various exemplary embodiments, the high torque level of the servomotor that ultimately causes actuation of end effector grip, which results in the relatively higher gripping force, may be about 1.5 Nm. The relatively high torque level of the motor and the relatively high gripping force of the end effector gripping device 700 are maintained at least through to the completion of the procedure, such as, e.g., a sealing procedure, a cutting procedure, etc. It is noted that the 0.3 Nm lower gripping force at the end effector and the 1.5 Nm higher gripping force at the end effector may be altered, depending on a desired slave gripping force. In another embodiment, the servomotor may actuate a clutch mechanism provided at the force/torque drive transmission mechanism 602, which actuates the end effector, increasing the gripping force at the end effector to the higher gripping force.

In some exemplary embodiments, a grip force torque control mechanism may be interfaced with the servomotor to ultimately control the delivery of the torque forces to actuate the end effector.

Reference is made to U.S. Provisional Application No. 61/491,804 (filed May 31, 2011; entitled "GRIP FORCE CONTROL IN A ROBOTIC SURGICAL INSTRUMENT"), the entire contents of which are incorporated herein by reference, for an exemplary embodiment of a vessel sealing and cutting instrument that utilizes a spring assembly in the transmission backend to transmit and control the torque from the servomotor that is delivered to the end effector. Those having ordinary skill in the art would appreciate that the control techniques described herein could be used in combination with such a transmission system.

The surgical procedure, such as sealing or cutting, may occur while both the additional input, such as the depression of one or more pedals 808, is actuated and the squeezing force at the master grip input levers 900*a*, 900*b* is maintained at or above the squeezing force threshold. At S4, the system senses the completion of the desired procedure and signals such to the user at the surgeon console 802, or at any location that would provide such an indication to a user, after which the user may be prompted to stop the master grip input by, for example, releasing the grip levers 900a, 900b. The surgical procedure, such as sealing, cutting or stapling, therefore ends at S4, indicated by the off state in the state diagram. The surgical procedure may be indicated by ending actuation of the seal, cut or staple input device (e.g., releasing one of the pedals 808), by recognizing, for example, that the tissue has been cut or by recognizing that the tissue has been sealed (e.g., by analyzing the conductance of the tissue), etc.

The surgical procedure may end when the user, e.g., the surgeon, releases the additional input device, such as, for example, one or more pedals 808. In another embodiment, the surgical procedure is performed until a processing device, such as an electrosurgical processing unit at, for example, the electronics/control console 804, senses that the procedure has been completed based on detecting information from the tissue. For example, the procedure may be sensed to have been completed when the tissue is determined to be less conductive after, for example, a sealing procedure. In another example, a cutting element position may be used to indicate that the procedure, such as a cutting procedure, is complete. One of ordinary skill in the art would recognize that the procedure may be performed only while the input device is actuated or may be performed upon actuation of the input device and ended after a processing device determines that the procedure may end, such as, for example, when the gripped tissue has been fully cut, after a designated amount of time has elapsed from the initiation of the surgical procedure, etc.

In the exemplary embodiment shown in FIG. 1A, the master grip input signal 100 is maintained in an on state after the surgical procedure ends at S4. The master grip input signal 100 can be maintained in the on state, for example, until a releasing threshold is sensed at the master grip levers 900a, 900b of the master grip input mechanism 806. The releasing threshold may be a releasing amount of release of the master grip levers 900a, 900b beyond a specific releasing amount and may provide a safety mechanism to ensure that a user is intending to stop a procedure that uses a relatively high gripping force. The releasing threshold may be approximately 20 percent or more of a releasing amount of the master grip levers 900a, 900b at the master grip input mechanism 806. In an exemplary embodiment, the releasing threshold may be about a 20% release of the second biasing mechanism of the master grip input mechanism 806 when the grip levers 900a, 900b have been released at S5. That is, the releasing threshold may be indicated by, for example, the release of the second biasing mechanism, such as second spring 904 shown in FIGS. 9A-9B, a bumper, etc., to a point that is indicative of the user's intent to release the grip, rather than a repositioning or shifting of the user's grip. For example, a release of the second biasing mechanism to a point 20% to 40% away from the fully closed/actuated position, may be indicative of an intentional release by the user. It should be understood that the release range is exemplary, and a specific range may be chosen based on the type of procedure, the type of grip used, the type of biasing mechanism used, and other factors. If the user, e.g., a surgeon, releases the master grip input levers 900a, 900b of the master grip input mechanism 806 at the surgeon console 802, when a processing device recognizes that the grip levers 900a, 900b have been released beyond the releasing threshold at S5, the slave gripping force 102 decreases from the high torque level indicative of a high grip at S5. The slave gripping force 102 may decrease from the higher torque level to the lower torque level or, in an alternative embodiment, may decrease from the higher torque level indicative of the high gripping force to no torque.

Figure 1B:
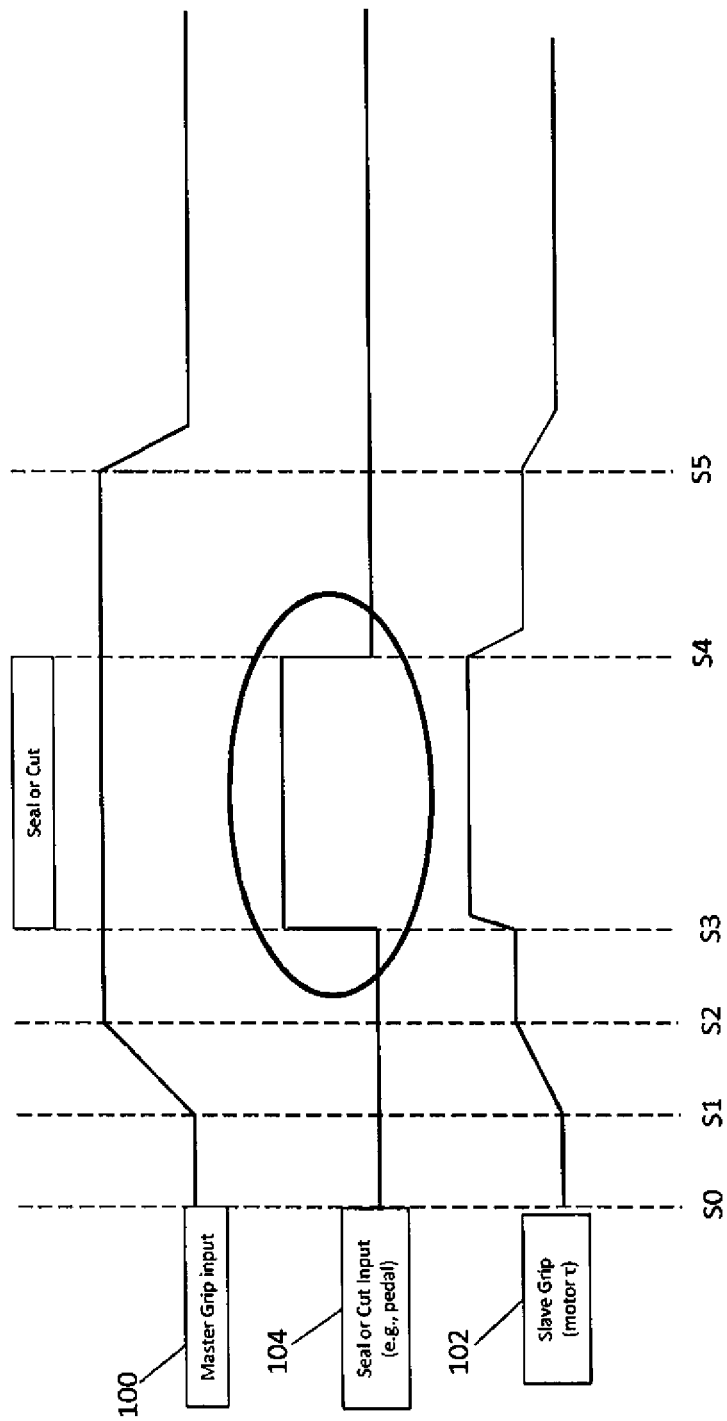
FIG. 1B is a state diagram depicting a gripping force control scheme for a robotically-controlled surgical instrument in accordance with another exemplary embodiment.

In an alternative embodiment, as shown in FIG. 1B, instead of remaining at the relatively high levels after the end of the surgical procedure at S4, the motor torque and corresponding slave gripping force 102 can automatically drop to a relatively low level when the surgical procedure is complete, but prior to the releasing threshold being reached.

Although FIGS. 1A and 1B show a sealing or cutting operation, one of ordinary skill in the art would understand that a combined sealing and cutting operation may occur.

Figure 2:
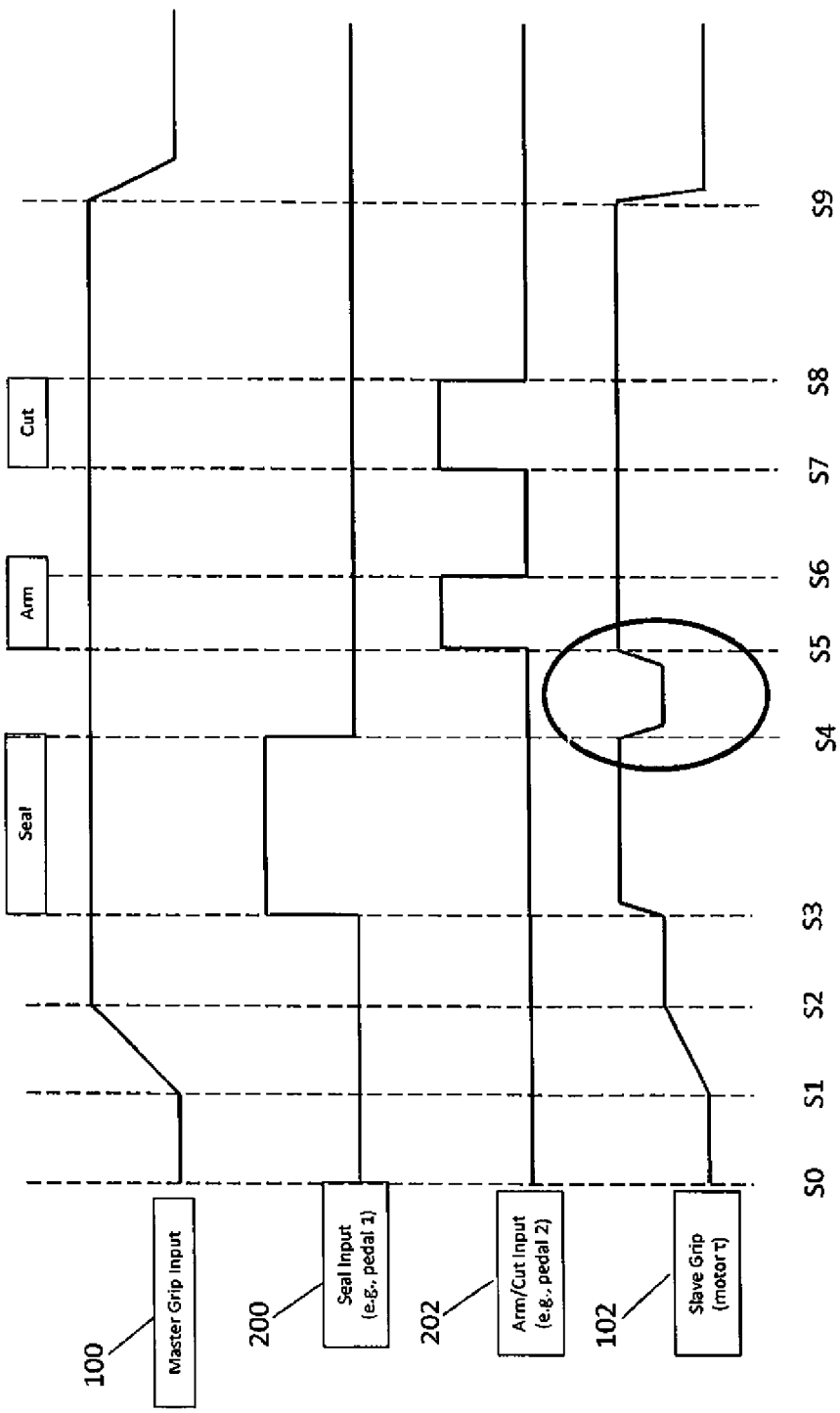
FIG. 2 is a state diagram depicting a gripping force control scheme for a robotically-controlled surgical instrument in accordance with at least one exemplary embodiment.

FIG. 2 is a state diagram of a method for controlling gripping force of a robotically-controlled surgical instrument end effector that performs a sealing procedure followed by a cutting procedure in accordance with another exemplary embodiment. FIG. 2 is similar to FIG. 1 at S0-S4 in relation to the master grip input 100, the slave gripping force 102 (which may be based on motor torque, for example), and the additional seal input 200. According to this embodiment, however, after the sealing procedure is performed at S3-S4, the motor torque and slave gripping force 102 return to a relatively low torque level at S4 until a subsequent operation, such as an arming operation which corresponds to a readiness of the user to perform a cutting procedure, occurs at S5. In an alternative embodiment, shown in FIG. 3, the slave gripping force 102 remains at the relatively high torque level from S4 to S5.

In order to provide an additional safety feature to prevent a surgeon from unintentionally performing a cutting procedure until the surgeon intends for the procedure to occur, at S5, the user provides a second additional input 202, for example through actuation of an input device, such as one or more of pedals 808 (which may be a different pedal, for example, than the pedal used for the additional seal input 200), to indicate a readiness to actuate the surgical instrument 600 to perform the cutting procedure, i.e., the surgical instrument is "armed". The "arming" state is indicated in the state diagram as the arm/cut input 202 transitioning from an off state at S4 to an on state at S5 in anticipation of a cutting procedure. When the arming input 202 has been received at S5, if the motor torque and slave gripping force 102 are at relatively low levels, as shown in FIG. 2, they increase to relatively high levels at S5 during the "arming" operation. Following the arming input by the user, an output signal can be output to provide feedback to the user that indicates that the user has "armed" the surgical instrument 600.

In the alternative, if the motor torque and slave gripping force 102 were not decreased between the sealing and arming stages at S3 and S5, respectively, then the relatively high levels can be maintained. The high motor torque and corresponding slave gripping force 102 can be maintained after the arming of the end effector 606 occurs at S5. The arm/cut input 202 transitioning from an on state at S5 to an off state at S6 in the state diagram indicates that the input to "arm" the surgical instrument 600 has ended.

After "arming" the surgical instrument 600, a user at the second additional input device, e.g., one or more of the pedals 808 at the surgeon console 802, provides another input to begin the cutting procedure at S7, which is indicated in the state diagram as the arm/cut input 206 transitioning from the off state at S6 to the on state at S7. After the cutting procedure ends, indicated by the arm/cut input 202 returning to an off state at S8, the motor torque may either be maintained at the relatively high torque level until the releasing threshold has been reached at S9, as shown in FIG.

2, or the motor torque may drop to the relatively low torque level or no torque immediately following the cutting operation.

For additional details regarding arming the surgical instrument prior to performing the cutting operation, reference is made to U.S. Provisional Patent Application No. 61/491,647 (filed on May 31, 2011; entitled "POSITIVE CONTROL OF ROBOTIC SURGICAL INSTRUMENT END EFFECTOR"), the entire contents of which are incorporated herein by reference.

It may be understood that while the exemplary embodiment of FIG. 2 indicates that the motor torque and slave gripping force 102 are maintained at the relatively high torque level from the initiation of the arming input at S5 through the beginning of the cutting operation at S7, in an alternative embodiment, they may decrease from a high torque level to a low torque level between the end of the arming input at S6 and the beginning of the cutting operation at S7. In another embodiment, the relatively low torque and slave gripping force levels can be maintained from the end of the sealing operation at S4 through the initiation of the cutting operation at S7. In yet another embodiment, the motor torque may be lowered to the low torque level after the sealing operation at S4, raised to the high torque level during the arming operation at S5, lowered to the low torque level after the end of the arming operation at S6 and then ultimately raised to the high torque level during the cutting operation at S7. It will be understand by those of ordinary skill in the art that any combination of torque and slave gripping force levels may be applied, with the exception of the sealing or cutting procedures which require the higher gripping force, and thus higher torque level, through the pendency of those procedures.

Figure 3:
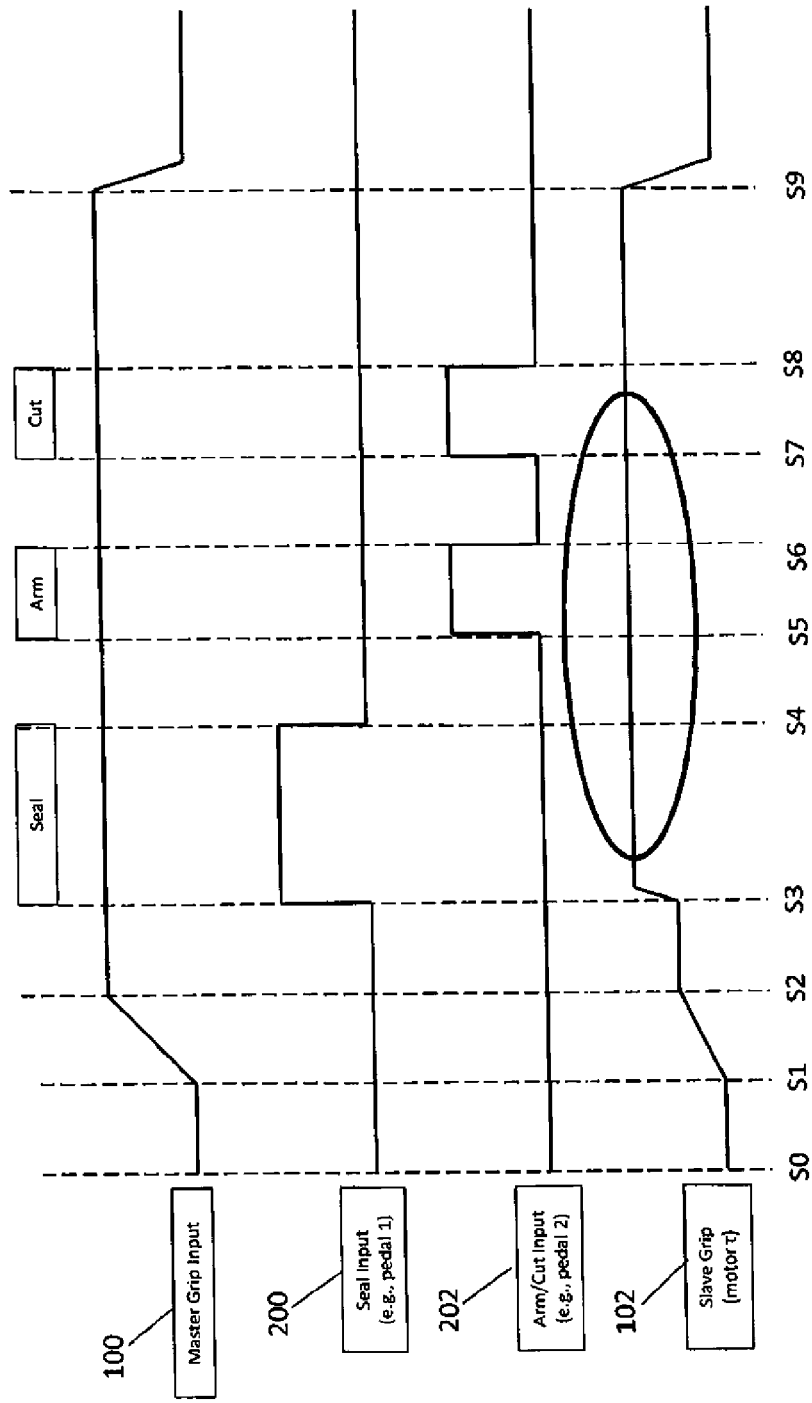
FIG. 3 is a state diagram depicting a gripping force control scheme for a robotically-controlled surgical instrument in accordance with at least one exemplary embodiment.

In addition, as shown in FIG. 3, the motor torque and slave gripping force 102 may be maintained at the relatively high levels from the initiation of the sealing operation at S3 through at least the end of the cutting operation at S8 and optionally until the releasing threshold has been achieved at S9.

Figure 4:
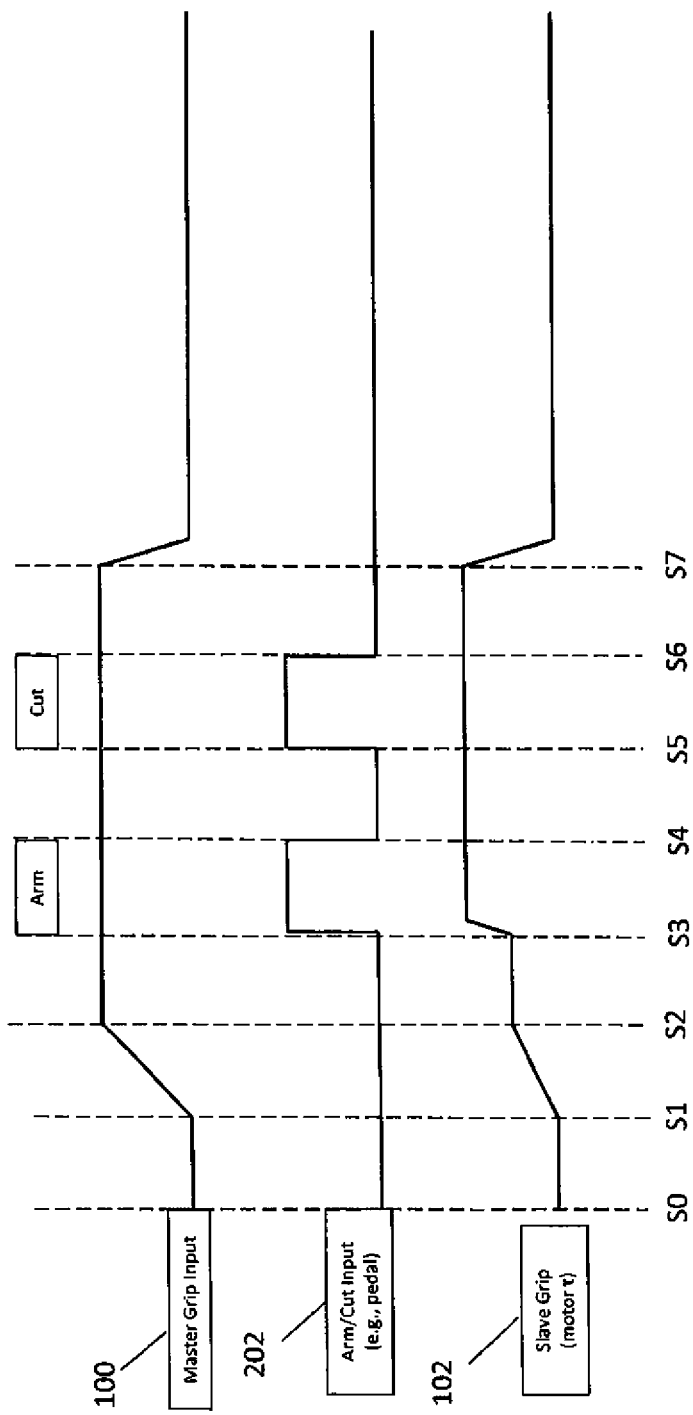
FIG. 4 is a state diagram depicting a gripping force control scheme for a robotically-controlled surgical instrument in accordance with at least one exemplary embodiment.

As shown in FIG. 4, in an exemplary embodiment, the sealing procedure may not be performed and only an arming and subsequent cutting procedure may be performed. The slave gripping force 102, controlled by the motor torque for example, may be increased at the arming operation at S3 to a relatively high level and maintained at the high level either through the pendency of the cutting operation at S6 or until the releasing threshold has been achieved at S7.

As mentioned above, in various exemplary embodiments, it may be desirable to control DOF movement of the surgical instrument, e.g., of the wrist and/or shaft, when performing various surgical procedures. Such control may be desirable, for example, to provide stability and/or other control over the surgical instrument during procedures that require high gripping force. Accordingly, various exemplary embodiments, contemplate locking and unlocking (i.e., allowing or preventing) one or more DOF movement of the surgical instrument depending on the state of the surgical instrument and the particular procedure being performed by the surgical instrument.

Figure 5:
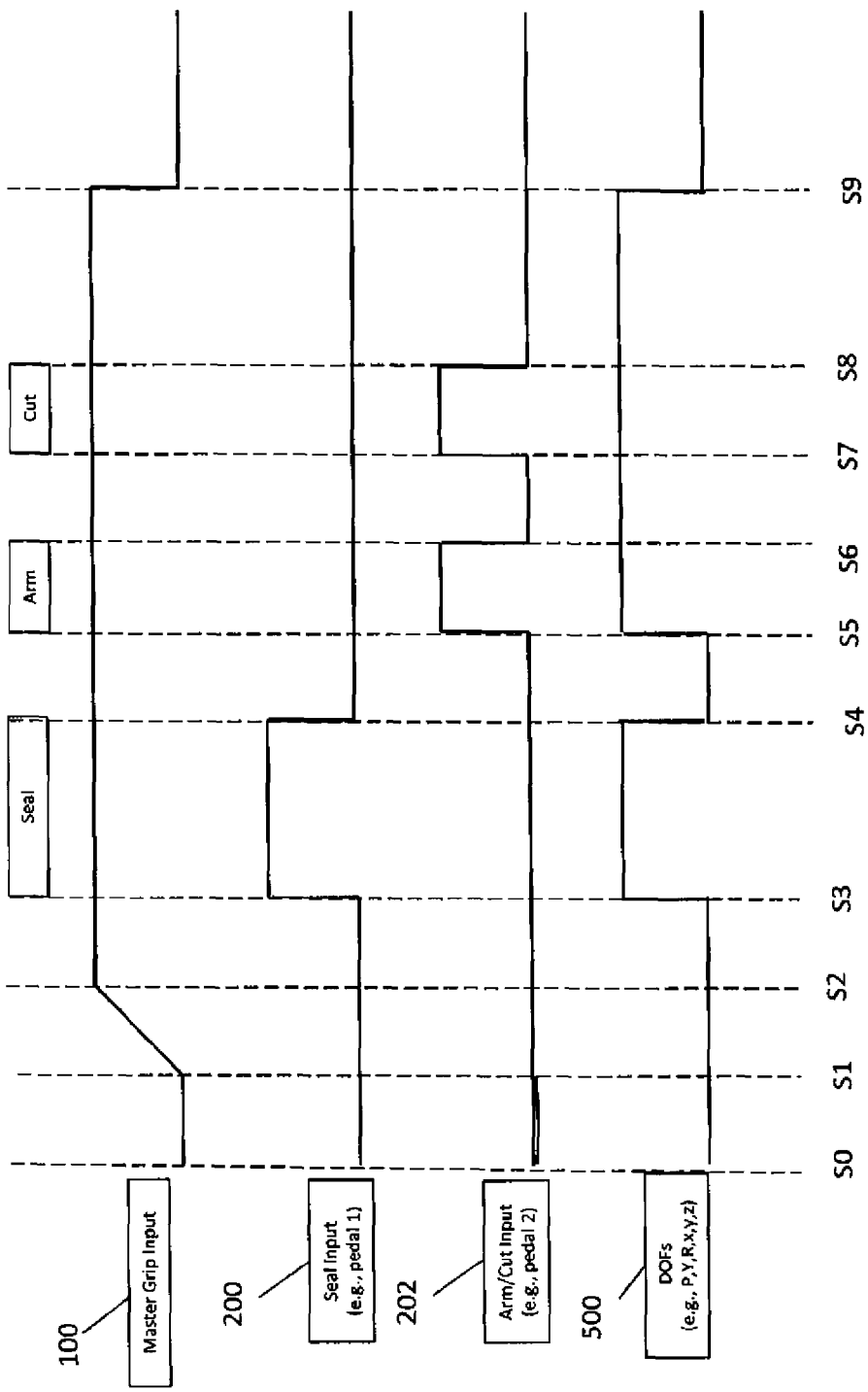
FIG. 5 is a state diagram depicting a gripping force control scheme for robotically-controlled surgical instrument in accordance with at least one exemplary embodiment.

Turning now to FIG. 5, a state diagram that depicts an exemplary control method, including control over the DOF movement of the surgical instrument, is depicted. The degrees of freedom (DOFs) of the surgical instrument, such as the pitch and yaw through the wrist mechanism 606, the roll through the shaft 604 and the movement of the instrument 600 in X, Y, and Z directions, which is controlled by the jointed arms 810 of the patient side cart 800, are locked or unlocked depending on, for example, the operation involved. For purposes of simplicity, the slave gripping force 102 has been omitted as the unlocking and locking of the DOFs 500 occurs independently of the operation of the slave gripping force 102.

At S3, when the sealing input is received and the master grip input is above the gripping force threshold, the DOFs 500 are locked, indicated by the transition from the off state at S2 to the on state at S3. When the sealing procedure ends at S4, the DOFs 500 may be unlocked to permit, for example, the surgeon to be able to manipulate the surgical instrument to move tissue or the like. In an alternative embodiment, the DOFs 500 may be maintained in a locked state following the sealing procedure at S4. Turning back to FIG. 5, when an input is received to indicate an armed state of the surgical instrument, at S5, if the DOFs 500 have been unlocked, the DOFs 500 are locked during the arming operation. The DOFs 500 may be locked through the end of arming at S6, through the initiation of cutting at S7, through the end of cutting at S8, and through until the releasing threshold has been achieved at S9.

In an alternative embodiment, the DOFs 500 may be unlocked from after the sealing procedure at S4 through the initiation of the cutting procedure at S7, whereupon the DOFs 500 are locked, i.e., the DOFs 500 are unlocked during the arming procedure. In another alternative embodiment, the DOFs 500 may be unlocked between each of the procedures, e.g., between S4 and S5, and between S6 and S7. Further, the DOFs 500 may be unlocked immediately following the cutting procedure at S8. Additionally, one or more DOFs 500 may be selectively locked or unlocked between procedures, e.g., the sealing or cutting procedures, and/or operations, e.g., the arming operation, or during the procedures or operations.

While the unlocking and locking of the DOFs 500 occurs independently of the higher and lower slave gripping forces at the end effector, the DOFs 500 are typically locked while the higher gripping force occurs at the end effector and the DOFs 500 are typically unlocked while the lower gripping force or the zero gripping force occurs at the end effector.

While procedures such as sealing and cutting have been disclosed, one of ordinary skill in the art would recognize that the present disclosure is not limited to the sealing and cutting procedures described and any of a variety of procedures that utilize a surgical instrument, e.g., stapling, etc. may be used.

Therefore, various exemplary embodiments in accordance with the present disclosure can provide a gripping force control scheme that increases a gripping force of an end effector gripping device to a higher level when two inputs indicative of an increased grip level and an initiation of a surgical procedure are both received. Further, various exemplary embodiments of the present disclosure also can enhance stability and control of a surgical instrument during a surgical procedure, even when relatively high gripping forces are used, by locking and unlocking various instrument DOF motions depending on the operational state of the surgical instrument.

The embodiments can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to effect the various responses and signal processing in accordance with various exemplary embodiments of the present disclosure can be implemented by a processor of or in conjunction with the electronics/control console 804, such as an electrosurgical processing unit discussed above, and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

As described above, the methods and systems in accordance with various exemplary embodiments can be used in conjunction with a surgical instrument having an end effector configured to perform multiple surgical procedures via components that are actuated via a transmission mechanism at the proximal end of the instrument. Further, according to an aspect of the embodiments, any combinations of the described features, functions and/or operations can be provided.

Other embodiments of the invention will be apparent to those skilled in the art from consideration of the specification and practice of the present disclosure and claims herein. It is intended that the specification and examples be considered as exemplary only, with a true scope and spirit of the invention being indicated by the following claims.

What is claimed is:

1. A method of controlling an end effector of a surgical instrument of a computer-assisted surgical system, the method comprising:
receiving a first input signal in response to a grip input at a master grip input mechanism, the master grip input mechanism being coupled to control a slave gripping force of an end effector of the surgical instrument;
receiving a second input signal after receiving the first input signal, wherein the second input signal is received in response to a procedure input at a master input device, the procedure input being different from the grip input at the master grip input mechanism, the procedure input being indicative of a user's readiness to operate the surgical instrument to perform a first surgical procedure; and
causing one or more degrees of freedom of the surgical instrument to be placed in a locked state in response to receiving the first input signal and the second input signal.

2. The method of claim 1, further comprising:
receiving an additional input signal indicative of a user's readiness to operate the surgical instrument to perform a subsequent surgical procedure; and
in response to receiving the additional input signal, causing the one or more degrees of freedom of the surgical instrument to be placed in an unlocked state between the first surgical procedure and the subsequent surgical procedure.

3. The method of claim 2, wherein receiving the second input signal comprises receiving an arming input signal indicative of the user's readiness to perform a cutting procedure.

4. The method of claim 3, further comprising:
receiving a cutting input signal after receiving the arming input signal, the cutting input signal indicating that the cutting procedure is to begin.

5. The method of claim 4, further comprising:
causing, between the arming operation and the cutting procedure, the one or more degrees of freedom of the surgical instrument to be placed in an unlocked state.

6. The method of claim 4, wherein the one or more degrees of freedom of the surgical instrument are maintained in a locked state between the arming operation and the cutting procedure.

7. The method of claim 1, further comprising:
outputting a first actuation signal causing the slave gripping force of the end effector to be increased to a first threshold level in response to receiving the first input signal; and
outputting a second actuation signal causing the slave gripping force of the end effector to be increased from the first threshold level to a second level higher than the first threshold level during the first surgical procedure in response to receiving at least the second input signal while continuing to receive the first input signal.

8. The method of claim 1, wherein receiving the first input signal occurs in response to the grip input at the master grip input mechanism meeting a squeezing force threshold.

9. The method of claim 8, further comprising:
providing haptic feedback to a user to indicate varying levels of squeezing force applied during the grip input at the master grip input mechanism.

10. The method of claim 1, further comprising:
outputting a first actuation signal, in reponse to receiving the first input signal, the first actuation signal causing an increase to a first threshold level of a torque of a drive input coupled to control the gripping force of the end effector; and
outputting a second actuation signal, in response to receiving the second input signal while continuing to receive the first input signal, the second actuation signal causing the torque of the drive input to increase from the first threshold level to a second level higher than the first threshold level during the first surgical procedure.

11. The method of claim 1, wherein one or more degrees of freedom of a shaft and/or a wrist of the surgical instrument are placed in a locked state during the first surgical procedure.

12. A method of controlling an end effector coupled to a shaft of a surgical instrument of a computer-assisted surgical system, the method comprising:
receiving a first input signal in response to grip input at a master grip input mechanism, the master grip input mechanism being coupled to control a slave gripping force of the end effector;
receiving a second input signal indicative of a user's readiness to operate the surgical instrument to perform a first surgical procedure; and
causing, in response to receiving the first and second input signals, one or more degrees of freedom of movement of at least one of the shaft and a wrist of the surgical instrument to be placed in a locked state during the first surgical procedure.

13. The method of claim 12, wherein the one or more degrees of freedom of movement of at least one of the shaft and a wrist of the surgical instrument includes articulation, roll, and/or translation of the shaft and/or wrist of the surgical instrument.

14. The method of claim 12, further comprising:
receiving an additional signal indicative of a user's readiness to operate the surgical instrument to perform a subsequent surgical procedure; and causing, in response to receiving the additional input signal, the one or more degrees of freedom of movement of the shaft and/or wrist of the surgical instrument to be placed in an unlocked state between the first surgical procedure and the subsequent surgical procedure.

15. The method of claim 12, wherein receiving the second input signal comprises receiving an arming input signal indicative of the user's readiness to perform a cutting procedure.

16. The method of claim 15, further comprising:
receiving a cutting input signal after receiving the arming input signal, the cutting input signal indicating that the cutting procedure is about to begin.

17. The method of claim 15, wherein the one or more degrees of freedom of movement of at least one of the shaft and wrist of the surgical instrument are maintained in the locked state between the arming operation and the cutting procedure.

18. The method of claim 12, further comprising:
outputting a first actuation signal causing the slave gripping force of the end effector to be increased to a first threshold level in response to receiving the first input signal; and
outputting a second actuation signal causing the slave gripping force of the end effector to be increased from the first threshold level to a second level higher than the first threshold level during the first surgical procedure in response to receiving at least the second input signal while continuing to receive the first input signal.

19. The method of claim 12, wherein receiving the first input signal occurs in response to the grip input at the master grip input mechanism meeting a squeezing force threshold.

20. The method of claim 19, further comprising:
providing haptic feedback to a user to indicate varying levels of squeezing force applied during the grip input at the master grip input mechanism.

21. The method of claim 19, wherein the squeezing force threshold is reached at 80 percent or more of a fully actuated position of the master grip input mechanism to actuate the slave gripping force.

22. The method of claim 12, further comprising:
outputting a first actuation signal, in response to receiving the first input signal, the first actuation signal causing an increase to a first threshold level of a torque of a drive input coupled to control the gripping force of the end effector; and
outputting a second actuation signal, in response to receiving the second input signal while continuing to receive the first input signal, the second actuation signal causing the torque of the drive input to increase from the first threshold level to a second level higher than the first threshold level during the first surgical procedure,
wherein receiving the second input signal comprises receiving an arming input signal in response to an arming input to arm the surgical instrument to perform a cutting procedure, and
wherein the second level of the torque of the drive input is maintained between arming of the surgical instrument and performance of the cutting procedure.

23. The method of claim 22, further comprising:
receiving an additional input signal, subsequent to completion of the first surgical procedure and indicative of a user's readiness to actuate the surgical instrument to perform a subsequent surgical procedure; and
outputting a signal to decrease the slave gripping force of the end effector between the first surgical procedure and the subsequent surgical procedure.

24. The method of claim 12, further comprising:
outputting a first actuation signal, in response to receiving the first input signal, to increase to a first threshold level a torque of a drive input coupled to control the slave gripping force of the end effector; and
outputting a second actuation signal, in response to receiving the second input signal while continuing to receive the first input signal, the second actuation signal causing the torque of the drive input to increase from the first threshold level to a second level higher than the first threshold level during the first surgical procedure.

* * * * *